United States Patent [19]
Whittaker et al.

[11] Patent Number: 5,637,595
[45] Date of Patent: Jun. 10, 1997

[54] CYCLIC ETHER ACETAL PAF ANTAGONISTS

[75] Inventors: Mark Whittaker; Andrew Miller; Stephen A. Bowles, all of Oxford, England

[73] Assignee: British Bio-technology Limited, England

[21] Appl. No.: 175,411

[22] PCT Filed: Jul. 1, 1992

[86] PCT No.: PCT/GB92/01189

§ 371 Date: Dec. 30, 1993

§ 102(e) Date: Dec. 30, 1993

[87] PCT Pub. No.: WO93/01191

PCT Pub. Date: Jan. 21, 1993

[30] Foreign Application Priority Data

Jul. 3, 1991 [GB] United Kingdom .............. 9114337

[51] Int. Cl.⁶ .............. C07D 471/04; C07D 405/12; A61K 31/44; A61K 31/425
[52] U.S. Cl. .............. 514/303; 514/234.2; 514/235.5; 514/236.8; 514/300; 514/336; 514/337; 514/374; 544/124; 544/127; 544/133; 546/118; 546/121; 546/280.1; 546/281.7; 546/282.1; 546/283.4; 548/203
[58] Field of Search .............. 546/121, 118, 546/268, 269, 283; 514/300, 303, 336, 337, 374; 248/203

[56] References Cited

U.S. PATENT DOCUMENTS

4,888,337  12/1989  Godfroid et al. .............. 514/326

FOREIGN PATENT DOCUMENTS

| | | |
|---|---|---|
| 0 144 804 A2 | 6/1985 | European Pat. Off. . |
| 0 199 324 A2 | 10/1986 | European Pat. Off. . |
| 0 238 202 A2 | 9/1987 | European Pat. Off. . |
| 0 353 777 A2 | 2/1990 | European Pat. Off. . |
| 0 381 098 A2 | 8/1990 | European Pat. Off. . |
| WO91/17157 | 11/1991 | WIPO . |

OTHER PUBLICATIONS

Whittaker et al. (1992), *Curr. Opin. Thera. Patents*, vol. 2, pp. 583–623.
Kishimoto CA 108: 221494 (EP 249170) Dec. 16, 1987.

*Primary Examiner*—Richard L. Raymond
*Attorney, Agent, or Firm*—Banner & Witcoff, Ltd.

[57] ABSTRACT

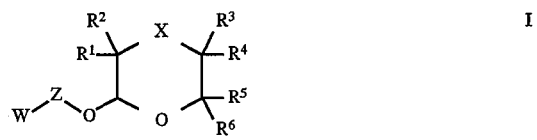

Compounds of general formula (I), wherein W represents a 5- or 6-membered aromatic heterocyclic ring containing one or more non-quaternised sp2 nitrogen atoms in its ring, which heterocyclic ring may be optionally fused to a benzene ring or to a further 5- or 6-membered aromatic heterocyclic ring containing one or more nitrogen atoms, wherein at least one of the said heterocyclic rings may also contain an oxygen or sulphur atom, and wherein any of the rings may be optionally substituted with one or more substituents selected from $-C_1-C_6$ alkyl, $-OC_1-C_6$ alkyl, halo, $-CF_3$ and $-CN$; Z represents a) a divalent alkanediyl group from 1 to 8 carbon atoms which may be a straight or branched-chain, wherein the said group is either unsubstituted or substituted by one or more substituents selected from hydroxy, $-OC_1-C_6$ alkyl, $-SC_1-C_6$ alkyl and halo; or b) a divalent alkenediyl or alkynediyl group from 2 to 8 carbon atoms which may be a straight or branched-chain, wherein the said group is either unsubstituted or subtituted by one or more substituents selected from hydroxy, $-OC_1-C_6$ alkyl, $-SC_1-C_6$ alkyl and halo; $R^1$, $R^2$, $R^3$, $R^4$, $R^5$, and $R^6$ each represents a hydrogen atom, a $-C_1-C_{18}$ alkyl or a $-C_2-C_{18}$ alkenyl group; or $R^3$ and $R^5$ together with the carbon atoms to which they are attached can form a five to ten membered monocycloalkyl or bicycloalkyl ring which may be optionally substituted with one or more substituents selected from $-C_1-C_6$ alkyl, $-OC_1-C_6$ alkyl, halo, $-CF_3$ and $-CN$; or $R^3$, $R^4$ and $R^5$, $R^6$ and the carbon atoms to which they are attached form a phenyl ring which may be optionally substituted with one or more substituents selected from $-C_1-C_6$ alkyl, $-OC_1-C_6$ alkyl, halo, $-CF_3$ and $-CN$; X represents a bond, an oxygen atom, a sulphur atom, a $-NH-$ group, a $-N(C_1-C_6\text{alkyl})-$ group, a $-(CH_2)_n-$ group or a $-CR^7R^8-$ group; n represents an integer of 1, 2 or 3; $R^7$ and $R^8$ each represents a $-C_1-C_{18}$ alkyl or a $-C_2-C_{18}$ alkenyl group; or $R^3$ and $R^7$ together with the carbon atoms to which they are attached can form a five to ten membered monocycloalkyl or bicycloalkyl ring which may be optionally substituted with one or more substituents selected from $-C_1-C_6$ alkyl, $-OC_1-C_6$ alkyl, halo, $-CF_3$ and $-CN$; or $R^3$, $R^4$ and $R^7$, $R^8$ and the carbon atoms to which they are attached form a phenyl ring which may be optionally substituted with one or more substituents selected from $-C_1-C_6$ alkyl, $-OC_1-C_6$ alkyl, halo, $-CF_3$ and $-CN$; and their pharmaceutically and veterinarily acceptable acid addition salts and hydrates are antagonists of platelet activating factor (PAF) and as such are useful in the treatment or amelioration of various diseases or conditions mediated by PAF.

16 Claims, No Drawings

5,637,595

CYCLIC ETHER ACETAL PAF ANTAGONISTS

This application is a 371 of PCT/GB92/01189 filed July 1, 1992. This invention relates primarily to novel compounds which are antagonists of platelet activating factor.

Platelet activating factor (PAF) is a bioactive phospholipid which has been identified as 1-O-hexadecyl/octadecyl-2-acetyl-sn-glyceryl-3-phosphoryl choline. PAF is released directly from cell membranes and mediates a range of potent and specific effects on target cells resulting in a variety of physiological responses which include hypotension, thrombocytopenia, bronchoconstriction, circulatory shock, and increased vascular permeability (oedema/erythema). It is known that these physiological effects occur in many inflammatory and allergic diseases and PAF has been found to be involved in a number of such disorders including asthma, endotoxin shock, adult respiratory distress syndrome, glomerulonephfitis, immune regulation, transplant rejection, gastric ulceration, psoriasis, cerebral, myocardial and renal ischemia. Thus the compounds of the invention, by virtue of their ability to antagonise the actions of PAF, should be of value in the treatment of any of the above conditions and any other conditions in which PAF is implicated (e.g. embryo implantation).

Compounds which have been disclosed as possessing activity as PAF antagonists include compounds which are structurally related to the PAF molecule such as glycerol derivatives (EP-A-0238202), and heterocyclic compounds such as 5-oxy derivatives of tetrahydrofuran (U.S. Pat. No. 4,888,337) and 2,5-diaryl tetrahydrofurans (EP-A-0144804). Recently a more potent 2,5-diaryl tetrahydrofuran derivative, (trans)-2-(3-methoxy-5-methylsulphonyl-4-propoxyphenyl)-5-(3,4,5-trimethoxyphenyl)tetrahydrofuran (L-659,989) has been disclosed (EP-A-0199324).

The compounds of the present invention differ from those such as L-659,989, in that they are substituted lactol ether derivatives rather than 2,5-diaryl tetrahydrofurans. The compounds of the present invention also differ from the 5-oxy derivatives of tetrahydofuran described in U.S. Pat. No. 4,888,337 in that they do not contain a quaternised nitrogen heterocycle and from the derivatives described in U.S. Pat. No. 4,888,337 in that they do not contain a quaternary ammonium group. The present invention provides novel and useful substituted lactol ether derivatives and their pharmaceutically acceptable acid addition salts, and pharmaceutical uses thereof as PAF antagonists.

According to a first aspect of the invention there is provided a compound of general formula I;

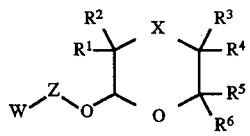

I wherein:

W represents a 5- or 6-membered aromatic heterocyclic ring containing one or more non-quaternised sp2 nitrogen atoms in its ting, which heterocyclic ring may be optionally fused to a benzene ring or to a further 5- or 6-membered aromatic heterocyclic ting containing one or more nitrogen atoms, wherein at least one of the said heterocyclic rings may also contain an oxygen or sulphur atom, and wherein any of the rings may be optionally substituted with one or more substituents selected from —$C_1$–$C_6$ alkyl, —$OC_1$–$C_6$ alkyl, halo, —$CF_3$ and —CN;

Z represents a) a divalent alkanediyl group from 1 to 8 carbon atoms which may be a straight or branched-chain, wherein the said group is either unsubstituted or substituted by one or more substituents selected from hydroxy, —$OC_1$–$C_6$ alkyl, —$SC_1$–$C_6$ alkyl and halo; or b) a divalent alkenediyl or alkynediyl group from 2 to 8 carbon atoms which may be a straight or branched-chain, wherein the said group is either unsubstituted or substituted by one or more substituents selected from hydroxy, —$OC_1$–$C_6$ alkyl, —$SC_1$–$C_6$ alkyl and halo;

$R^1$, $R^2$, $R^3$, $R^4$, $R^5$, and $R^6$ each represents a hydrogen atom, a —$C_1$–$C_{18}$ alkyl or a —$C_2$–$C_{18}$ alkenyl group;

or $R^3$ and $R^5$ together with the carbon atoms to which they are attached can form a five to ten membered monocycloalkyl or bicycloalkyl ring which may be optionally substituted with one or more substituents selected from —$C_1$–$C_6$ alkyl, —$OC_1$–$C_6$ alkyl, halo, —$CF_3$ and —CN;

or $R^3$, $R^4$ and $R^5$, $R^6$ and the carbon atoms to which they are attached form a phenyl ring which may be optionally substituted with one or more substituents selected from —$C_1$–$C_6$ alkyl, —$OC_1$–$C_6$ alkyl, halo, —$CF_3$ and —CN;

X represents a bond, an oxygen atom, a sulphur atom, a —NH— group, a —N($C_1$–$C_6$ alkyl)— group, a —$(CH_2)_n$— group or a —$CR^7R^8$— group;

n represents an integer of 1, 2 or 3;

$R^7$ and $R^8$ each represents a —$C_1$–$C_{18}$ alkyl or a —$C_2$–$C_{18}$ alkenyl group;

or $R^3$ and $R^7$ together with the carbon atoms to which they are attached can form a five to ten membered monocycloalkyl or bicycloalkyl ring which may be optionally substituted with one or more substituents selected from —$C_1$–$C_6$ alkyl, —$OC_1$–$C_6$ alkyl, halo, —$CF_3$ and —CN;

or $R^3$, $R^4$ and $R^7$, $R^8$ and the carbon atoms to which they are attached form a phenyl ring which may be optionally substituted with one or more substituents selected from —$C_1$–$C_6$ alkyl, —$OC_1$–$C_6$ alkyl, halo, —$CF_3$ and —CN;

or a pharmaceutically or veterinarily acceptable acid addition salt or hydrate thereof.

As used herein the term "halo" means fluoro, chloro, bromo or iodo.

As used herein the term "$C_1$–$C_{18}$ alkyl" refers to straight chain or branched chain hydrocarbon groups having from one to eighteen carbon atoms. Illustrative of such alkyl groups are methyl, ethyl, propyl, isopropyl, butyl, isobutyl, sec-butyl, tert-butyl, pentyl, neopentyl, hexyl, decyl, dodecyl, tridecyl, tetradecyl, pentadecyl, hexadecyl, heptadecyl, and octadecyl. From one to eight carbon atoms may be preferred.

As used herein the term "$C_2$–$C_{18}$ alkenyl" refers to straight chain or branched chain hydrocarbon groups having from two to eighteen carbon atoms and having in addition one or more double bonds, of either E or Z stereochemistry where applicable. This term would include for example, vinyl, 1-propenyl, 1- and 2-butenyl, 2-methyl-2-propenyl, geranyl, and farnesyl. From two to eight carbon atoms may be preferred.

As used herein the term "$OC_1$–$C_6$ alkyl" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "non-quaternised sp2 nitrogen atoms" refers to heterocyclic nitrogen atoms but does not include heterocyclic nitrogen atoms which are N-oxides.

As used herein the term "five to ten membered monocycloalkyl or bicycloalkyl ring" refers to an alicyclic group having from 5 to 10 carbon atoms. Illustrative of such cycloalkyl groups are cyclopropyl, cyclobutyl, cyclopentyl, cyclohexyl, cycloheptyl, cyclooctyl, cyclononyl, cyclodecyl and decahydronaphthyl.

Hereafter in this specification the term "compound" includes "salt" or "hydrate" unless the context requires otherwise.

In compounds of this invention, the presence of several asymmetric carbon atoms gives rise to diastereoisomers, each of which consists of two enantiomers, with the appropriate R or S stereochemistry at each chiral centre. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

Preferred compounds include those in which, independently or in any compatible combination:

W represents a pyridyl (for example 2-pyridyl or 3-pyridyl) group, a thiazolyl (for example 4-methylthiazol-5-yl) group or more preferably an imidazo[4,5-c]pyrid-1-yl (for example 2-methyiimidazo[4,5-c]pyrid-1-yl) group;

Z represents an alkanediyl (for example methylene, ethylene and propylene) group;

$R^1$ represents a hydrogen atom;

$R^2$ represents a hydrogen atom;

$R^3$ represents a hydrogen atom;

$R^4$ represents a hydrogen atom;

$R^5$ represents a hydrogen atom or together with $R^3$ and the carbon atoms to which they are attached form a five to ten membered monocycloalkyl or bicycloalkyl (for example decahydronaphthyl) ring;

$R^6$ represents a hydrogen atom or a —$C_1$-$C_{18}$ alkyl (for example methyl, ethyl, n-butyl and n-heptyl) group;

X represents a bond or a —$(CH_2)n$— group;

n represents an integer of 1;

$R^7$ and $R^8$ represent together with $R^3$ and $R^4$ and the carbon atoms to which they are attached a phenyl (for example dimethoxybenzene) ring;

Particularly preferred compounds include:

1. O-(3-(2-Methylimidazo[4,5-c]pyrid-1-yl)propyl)-5-n-heptyl-delta-valerolactol ether,
2. O-(3-(2-Methylimidazo[4,5-c]pyrid-1-yl)propyl)-5-n-heptyl-gamma-butyrolactol ether,
3. O-(3-(3-Pyridyl)propyl)-5-n-heptyl-gamma-butyrolactol ether.
4. O-(3-(2-Methylimidazo[4,5-c]pyrid-1-yl)propyl)-5-n-ethyl-gamma-butyrolactol ether
5. O-(3-(3-Pyridyl)propyl)-5-n-butyl-gamma-butyrolactol ether,
6. O-2-Pyridylmethyl-5-n-butyl-gamma-butyrolactol ether,
7. O-(3-(3-Pyridyl)propyl)-5-n-heptyl-delta-valerolactol ether,
8. O-2-(4-Methylthiazol-5-yl)ethyl-5-n-butyl-gamma-butyrolactol ether,
9. 2-(3-(3-Pyridyl)propoxy-3a,6,6,9a-tetramethyldodecahydronaphtho[2,1-b]furan,
10. O-2-(4-Methylthiazol-5-yl)ethyl-6,7-dimethoxyisochroman-3-ol ether,
11. O-(3 -(2-Methylimidazo[4,5-c]pyrid-1-yl)propyl)-delta-valerolactol ether.

Compounds of general formula I may be prepared by any suitable method known in the art and/or by the following process, which itself forms part of the invention.

According to a second aspect of the invention, there is provided a process for preparing a compound of general formula I as defined above, the process comprising:

a) treating a lactol derivative represented by the general formula II

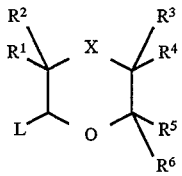

wherein $R^1$, $R^2$, $R^3$, $R^4$, $R^5$, $R^6$ and X are as defined in general formula I and L is fluoro, chloro, bromo, iodo, hydroxy, —$OC_1$-$C_6$ alkyl, benzoxy, acetoxy, —OC(NH)$CCl_3$, —$SO_2Ph$, —$SC_1$-$C_6$ alkyl or —SPh with an alcohol of the general formula III

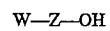

wherein W and Z are as defined in general formula I;

b) treating a lactol derivative represented by the general formula II, wherein $R^1$, $R^2$, $R^3$, $R^4$, $R^5$, $R^6$ and X are as defined in general formula I and L is hydroxy with a halide of general formula IV

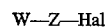

wherein W and Z are as defined in general formula I and Hal is fluoro, chloro, bromo or iodo;

c) treating an unsaturated lactol derivative represented by the general formula V

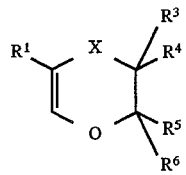

wherein $R^1$, $R^3$, $R^4$, $R^5$, $R^6$ and X are as defined in general formula I with an alcohol of general formula III and an acid catalyst;

d) reducing an unsaturated lactol ether of general formula VI

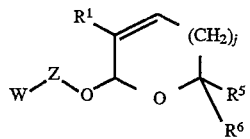

wherein W, Z, $R^1$, $R^5$, and $R^6$ are as defined in general formula I and j is an integer from 1 to 3; or e) treating a sulphonyl cyclic ether of general formula VII

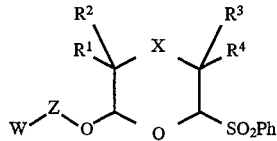

wherein W, Z, $R^1$, $R^2$, $R^3$, $R^4$ and X are as defined in general formula I, with a Grignard reagent of general formula VIII R⁶MgBr    VIII wherein R⁶ is as defined in general formula I but is not hydrogen; and f) optionally after any of steps (a) to (e) convening a compound of general formula I so formed into another compound of general formula I.

The preferred reaction conditions for step (a) vary with the nature of the L group. When the L group is fluoro, chloro, bromo or iodo the reaction may be conducted with an appropriate silver salt (e.g. silver oxide or silver carbonate) and a drying agent (e.g. anhydrous calcium sulphate) either in neat alcohol of general formula III or with one or more equivalents of alcohol of general formula III in an appropriate anhydrous solvent (e.g. acetone). Alternatively, the reaction may be conducted in the presence of a base (e.g. potassium hydroxide) in an appropriate solvent (e.g. acetone). When the L group is hydroxy, —OC₁–C₆ alkyl, benzoxy, acetoxy, —OC(NH)CCl₃, the reaction may be conducted with an appropriate Bronsted or Lewis acid catalyst (e.g. p-toluene sulphonic acid, DOWEX 50(H⁺), boron trifluoride etherate, zinc chloride) either in neat alcohol of general formula III or with one or more equivalents of alcohol of general formula III in an appropriate anhydrous solvent (e.g. dichloromethane). (The word DOWEX is a trademark). When the L group is —SO₂Ph the reaction may be conducted with two equivalents of magnesium bromide etherate and one equivalent of solid sodium bicarbonate in tetrahydrofuran. When the L group is —SPh the reaction may be conducted with a suitable activating agent (e.g. bromine, N-bromosuccinimide, N-iodosuccinimide, dimethyl(methylthio)sulphonium trifluoromethane sulphonate). The above reactions can be effected at mild temperatures, typically between 0° C. and 50° C.

The reaction of step (b) can for preference be conducted with a silver salt (e.g. silver oxide) in an aprotic solvent (e.g. acetone).

The reaction of step (c) can for preference be conducted with catalytic p-toluenesulphonic acid or pyridinium p-toluenesulphonate in dichloromethane.

The reaction of step (d) can for preference be conducted with hydrogen in the presence of a suitable catalyst (eg 10% palladium in charcoal).

The reaction of step (e) can for preference be conducted in the presence of anhydrous zinc bromide in dry tetrahydrofuran.

The products of general formula I, obtained from step (a), (b), (c), (d), or (e) will be mixtures of one or more pairs of diastereoisomers. These may be separated by physical methods (e.g. flash chromatography).

Lactol derivatives of general formula II may be prepared by a number of methods. The first method for the preparation of lactol derivatives of general formula II, wherein L is hydroxy, involves treatment of an acetal of general formula IX

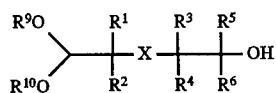

wherein $R^1$, $R^2$, $R^3$, $R^4$, $R^5$, $R^6$ and X are as defined in general formula I and each of $R^9$ and $R^{10}$ represents a —C₁–C₆ alkyl group or $R^9$ and $R^{10}$ together with the oxygen atoms to which they are attached form a 5- or 6-membered ring, with aqueous mineral acid (e.g. 20% sulphuric acid).

Acetals of general formula IX may be prepared by the reaction of a carbonyl compound of general formula X

R⁵—CO—R⁶    X wherein $R^5$, and $R^6$ are as defined in general formula I, with a Grignard reagent of general formula XI

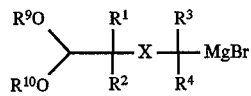

wherein $R^1$, $R^2$, $R^3$, $R^4$ and X are as defined in general formula I and $R^9$ and $R^{10}$ are defined in general formula IX, in an ethereal solvent (e.g. tetrahydrofuran) at 25° C. Carbonyl compounds of general formula X are available in the art or may be prepared by methods analogous to those known in the art. Grignard reagents of general formula XI can be prepared by methods known to those skilled in the art, or from materials known in the art.

In a second method lactol derivatives of general formula II, wherein L is hydroxy, may be prepared by the reduction of a lactone of general formula XII

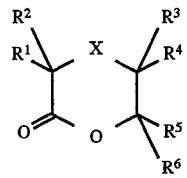

wherein $R^1$, $R^2$, $R^3$, $R^4$, $R^5$, $R^6$ and X are as defined in general formula I, with a suitable reducing agent (e.g. diisobutylaluminium hydride) in an appropriate solvent (e.g. toluene).

Lactones of general formula XII are available in the art or may be prepared by methods known to those skilled in the art, which include the following procedures. The first method involves cyclisation of a hydroxy ester of general formula XIII

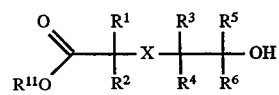

wherein $R^1$, $R^2$, $R^3$, $R^4$, $R^5$, $R^6$ and X are as defined in general formula I and $R^{11}$ is —C₁–C₆ alkyl, catalysed by a suitable acid (e.g. p-toluenesulphonic acid).

Hydroxy esters of general formula XIII, wherein $R^5$ is a hydrogen atom, may be prepared by the reduction of keto esters of general formula XIV

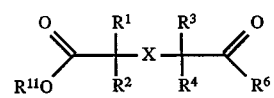

wherein $R^1$, $R^2$, $R^3$, $R^4$, $R^6$ and X are as defined in general formula I and $R^{11}$ is as defined above, with a suitable reducing agent (e.g. sodium borohydride). Under certain conditions (sodium cyanoborohydride and hydrochloric acid in tetrahydrofuran at reflux) keto esters of general formula XIV may be convened directly to lactones of general formula XII. Optically active enantiomers of hydroxy esters of general formula XIII may be obtained by utilising a chiral reducing agent (e.g. Bakers' yeast) for the reduction of keto esters of general formula XIV. Keto esters of general formula XIV are available in the art or may be prepared by methods analogous to those known in the art.

In a second method lactones of general formula XII, wherein n is an integer of 0, may be prepared by the treatment of an unsaturated ester of general formula XV

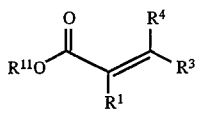

wherein $R^3$, and $R^4$ are as defined in general formula I and $R^{11}$ is as defined in general formula XIII, with a carbonyl compound of general formula X wherein $R^5$, and $R^6$ are as defined in general formula I, with samarium iodide in tetrahydrofuran. Unsaturated esters of general formula XV are available in the art or may be prepared by methods analogous to those known in the art.

Optionally after either of the above methods, a lactone of general formula XII may be converted into another lactone of general formula XII, in one or a plurality of the following methods:

i) by treatment of a lactone of general formula XII, wherein $R^1$, $R^2$, $R^3$, $R^4$, $R^5$ and X are as defined in general formula I and $R^6$ is a hydrogen atom with a strong organic non nucleophilic base (e.g. lithium diisopropyl amide) followed by a compound of general formula XVI $$R^1 A \qquad XVI$$

wherein $R^1$ represents a —$C_1$–$C_{18}$ alkyl or —$C_2$–$C_{18}$ alkenyl group and A is chloro, bromo, iodo, methanesulphonyloxy, p-toluenesulphonyloxy or trifluoromethanesulphonyloxy; and/or ii) by treatment of a lactone of general formula XII, wherein X is a bond, $R^2$, $R^3$, $R^5$ and $R^6$ are as defined in general formula I and each of $R^1$ and $R^4$ is a hydrogen atom with a strong organic non-nucleophilic base (e.g. lithium diisopropyl amide) followed by a compound of general formula XVII $$PhSeCl \qquad XVII$$

subsequent treatment with hydrogen peroxide to yield an unsaturated lactone to which is added an appropriate organometallic reagent for example of general formula XVIII $$(R^4)_2 CuLi \qquad XVIII$$

wherein $R^4$ is as defined in general formula I.

In a third method lactol derivatives of general formula II, wherein L is —$OC_1$–$C_6$ alkyl, may be prepared by the treatment of a sulphone of general formula XIX

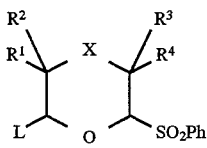

wherein $R^1$, $R^2$, $R^3$, $R^4$ and X are as defined in general formula I and L is —$OC_1$–$C_6$ alkyl, with a Grignard reagent of general formula XX $$R^6 MgBr \qquad XX$$

wherein $R^6$ is as defined in general formula I in the presence of anhydrous zinc bromide in dry tetrahydrofuran.

Sulphones of general formula XIX may be prepared by the reaction of a cyclic ether of general formula XXI

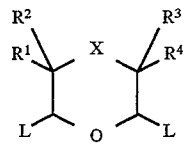

wherein $R^1$, $R^2$, $R^3$, $R^4$ and X are as defined in general formula I and L is —$OC_1$–$C_6$ alkyl, with one equivalent of benzenesulphinic acid and powdered calcium chloride in dichloromethane. Cyclic ethers of general formula XXI are available in the art or may be prepared by methods analogous to those known in the art.

Optionally, after the above methods, a lactol of general formula II may be converted into another lactol of general formula II, in one or a plurality of the following methods:

i) by treatment of a lactol derivative of general formula II, wherein $R^1$, $R^2$, $R^3$, $R^4$, $R^5$, $R^6$ and X are as defined in general formula I and L is —$OC_1$–$C_6$ alkyl, with benzenesulphinic acid and powdered anhydrous calcium chloride in dichloromethane to give a lactol derivative of general formula II wherein $R^1$, $R^2$, $R^3$, $R^4$, $R^5$, $R^6$ and X are as defined in formula I and L is $SO_2Ph$;

ii) by treatment of a lactol derivative of general formula II, wherein $R^1$, $R^2$, $R^3$, $R^4$, $R^5$, $R^6$ and X are as defined in formula I and L is hydroxy, with $NCCCl_3$ and sodium hydride in dichloromethane at room temperature to give a lactol derivative of general formula II wherein $R^1$, $R^2$, $R^3$, $R^4$, $R^5$, $R^6$ and X are as defined in formula I and L is —$OC(NH)CCl_3$;

iii) by treatment of a lactol derivative of general formula II, wherein $R^1$, $R^2$, $R^3$, $R^4$, $R^5$, $R^6$ and X are as defined in formula I and L is —$C_1$–$C_6$ alkyl, with $PhSSiMe_3$ in the presence of either trimethylsilyltriflate in dichloromethane or anhydrous zinc iodide and tetrabutylammonium iodide in 1,2-dichloroethane to give a lactol derivative of general formula II wherein $R^1$, $R^2$, $R^3$, $R^4$, $R^5$, $R^6$ and X are as defined in formula I and L is SPh;

iv) by treatment of a lactol derivative of general formula II, wherein $R^1$, $R^2$, $R^3$, $R^4$, $R^5$, $R^6$ and X are as defined in formula I and L is hydroxy or acetoxy, with a hydrogen halide in acetic anhydride to give a lactol derivative of general formula II wherein $R^1$, $R^2$, $R^3$, $R^4$, $R^5$, R6 and X are as defined in formula I and L is fluoro, chloro, bromo or iodo; and/or v) by treatment of a lactol derivative of general formula II, wherein $R^1$, $R^2$, $R^3$, $R^4$, $R^5$, $R^6$ and X are as defined in formula I and L is hydroxy, with acetic anhydride and anhydrous zinc halide to give a lactol derivative of general formula II wherein $R^1$, $R^2$, $R^3$, $R^4$, $R^5$, $R^6$ and X are as defined in formula I and L is chloro, bromo or iodo.

Alcohols of general formula III are either known compounds or can be prepared conventionally (e.g. by the methods described for the preparation of the Examples).

Halides of general formula IV are available in the art or can be prepared by methods known to those skilled in the art.

Unsaturated cyclic ether derivatives of general formula V may be prepared by the pyrolysis of lactol esters of general formula XXII

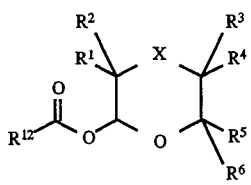

XXII wherein $R^1$, $R^2$, $R^3$, $R^4$, $R^5$, $R^6$ and X are as defined in formula I and $R^{12}$ is —$C_1$–$C_6$ alkyl. Lactol esters of general formula XXII may be prepared from lactol derivatives of general formula II wherein L is hydroxy by methods known to those skilled in the art.

Sulphonyl cyclic ethers of general formula VII may be prepared by the treatment of a bis-sulphone of general formula XXIV

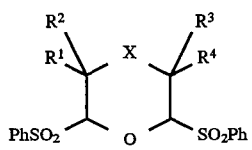

XXIV wherein $R^1$, $R^2$, $R^3$, $R^4$ and X are as defined in general formula I, with an alcohol of general formula III in the presence of two equivalents of magnesium bromide etherate and one equivalent of solid sodium bicarbonate in tetrahydrofuran.

Bis-sulphones of general formula XXIV may be prepared by treating a cyclic ether of general formula XXI with benzenesulphinic acid and calcium chloride in dichloromethane.

The appropriate solvents employed in the above reactions are solvents wherein the reactants are soluble but do not react with the reactants. The preferred solvents vary from reaction to reaction and are readily ascertained by one of ordinary skill in the art.

Compounds of general formulae II, V, VI, and VII are valuable intermediates in the preparation of compounds of general formula I, as are other novel compounds specifically or generically disclosed herein.

This invention also relates to a method of treatment for patients (or animals including mammalian animals raised in the dairy, meat, or fur trade or as pets) suffering from disorders or diseases which can be attributed to PAF as previously described, and more specifically, a method of treatment involving the administration of PAF antagonists of general formula I as the active ingredient. In addition to the treatment of warm blooded animals such as mice, rats, horses, cattle, pigs, sheep, dogs, cats, etc., the compounds of the invention are effective in the treatment of humans.

According to a third aspect of the invention there is provided a compound of general formula I for use in human or veterinary medicine particularly in the management of diseases mediated by PAF; compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immune complex deposition and smooth muscle contractions.

According to a fourth aspect of the invention there is provided the use of a compound of general formula I in the preparation of an agent for the treatment of PAF-mediated diseases; and/or the treatment of inflammation such as rheumatoid arthritis, osteoarthritis and eye inflammation, cardiovascular disorder, thrombocytopenia, asthma, endotoxin shock, glomerulonephritis, immune regulation, psoriasis.

Compounds of general formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to a fifth aspect of the invention there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of general formula I may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid nonionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 10 to 100 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of general formula I exhibit in vitro. antagonistic activities with respect to PAF. Compounds of general formula I inhibit PAF-induced functions in both the cellular and tissue levels by changing the PAF binding to its specific receptor site. The ability of compounds of general formula I to inhibit the binding of PAF to its specific receptor binding site on human platelet plasma membranes was measured according to Example 13. The ability of compounds of general formula I to inhibit PAF-induced hypotension in rats was measured according to Example 14.

The following examples illustrate the invention, but are not intended to limit the scope in any way.

The following abbreviations have been used in the Examples:-

DCM - Dichloromethane
DIPE - Diisopropylether
NBS - N-Bromosuccinimide
THF - Tetrahydrofuran

EXAMPLE 1

O-(3-(2-Methylimidazo[4,5-c]pyrid-1-yl)propyl)-5-n-heptyl-delta-valerolactol ether

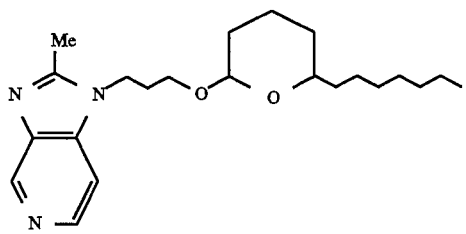

(a) 4-(3-Hydroxypropylamino)-3-nitropyridine

3-Amino-1-propanol (4.5 g, 60.0 mmol) was added slowly to a mixture of 4-chloro-3-nitropyridine (8.0 g, 50.5 mmol) and sodium hydrogen carbonate (4.2 g, 50.0 mmol) in ethanol (200 ml). The mixture was stirred for 3 h at ambient temperature and the solvent removed under reduced pressure. Saturated aqueous sodium hydrogen carbonate (50 ml) was added to the residue, which was extracted with ethyl acetate (3×200 ml). The combined organics were dried over anhydrous sodium sulphate, filtered and evaporated. Crystallisation from ethyl acetate gave 4-(3-hydroxypropylamino)-3-nitropyridine (4.3 g, 43%) as an orange crystalline solid.

delta$_H$ (250 MHz, CDCl$_3$) 9.20 (1H, s), 8.48 (1H, br s), 8.28 (1H, d), 6.78 (1H, d), 3.86 (2H, t), 3.53 (2H, q), 2.08 (1H, br s), 2.03 (2H, m).

(b) 3-Amino-4-(3-hydroxypropylamino)pyridine 4-(3-Hydroxypropylamino)-3-nitropyridine (4.12 g, 20.9 mmol) was dissolved in ethanol (130 ml) and Raney nickel (411 mg, 7.0 mmol) added. The stirred mixture was hydrogenated for 3 days. The catalyst was removed by filtration under argon and the solvent removed under reduced pressure to give 3-amino-4-(3- hydroxypropylamino)pyridine as a brown oil which was used directly in the next step.

(c) 1-(3-Acetoxypropyl)-2-methylimidazo[4,5-c]pyridine

Crude 3-amino-4-(3-hydroxypropylamino)pyridine (4.5 g, 27 mmol) was dissolved in acetic anhydride (56 ml) and the mixture heated at reflux overnight. The excess acetic anhydride was removed under reduced pressure and the residue purified by column chromatography (flash silica gel; 5%–50% methanol in DCM) to give 1-(3-acetoxypropyl)-2-methylimidazo[4,5-c]pyridine (1.81 g, 29%) as a colourless oil.

delta$_H$ (250 MHz, CDCl$_3$) 8.98 (1H, s), 8.35 (1H, d), 7.23 (1H, d), 4.23 (2H, t), 4.08 (2H, t), 2.63 (3H, s), 2.13 (2H, m), 2.03 (3H, s).

(d) 3 -( 1H-2-Methylimidazo[4,5-c]pyridyl)-1-propanol

To a solution of 1-(3-Acetoxypropyl)-2-methylimidazo[4,5-c]pyridine (1.8 g, 7.8 mmol) in ethanol (40 ml), was added slowly aqueous 2M potassium hydroxide (7 ml, 14 mmol) and the resulting mixture stirred for 3 h at room temperature. The solvent was removed under reduced pressure and the residue was treated with 2M hydrochloric acid (50 ml). The solution was washed with DCM (2×100 ml), solid sodium hydrogen carbonate added to pH 7.5, before extraction with DCM (10x100 ml). The combined organics were dried over anhydrous sodium hydrogen carbonate, filtered and evaporated to give 3-(1H-2-methylimidazo[4,5-c]pyridyl)-1-propanol (1.21 g, 82%) as a light brown oil.

delta$_H$ (250 MHz, CDCl$_3$) 8.88 (1H, s), 8.25 (1H, d), 7.33 (1H, d), 4.30 (2H t), 3.63 (2H, t), 2.63 (3H, s), 2.04 (2H, m).

(e) delta-Dodecanolactol

A 1.5M solution of diisobutylaluminium hydride in toluene (28.5 ml, 43 mmol) was added to a stirred solution of delta-dodecanolactone (6.0 ml, 29 mmol) in dry THF (50 ml) at −78° C. under argon. The mixture was stirred for 30 min. at −78° C. and 1M aqueous sodium hydroxide (1 ml) added. The mixture was allowed to warm to room temperature and was filtered through celite, diluted with ethyl acetate (150 ml) and washed with brine (2×50 ml). The organics were dried over anhydrous sodium sulphate, filtered and evaporated. Chromatography (silica: 25% ethyl acetate in hexane) gave delta-dodecanolactol (2.95 g, 52%) as a colourless oil.

delta$_H$ (250 MHz, CDCl$_3$) 5.21 (0.5H, br s), 4.72 (0.5H, br s), 4.67–4.53 (0.5H, m), 4.15 (0.5H, br s), 3.94–3.78 (0.5H, m), 3.40–3.26 (0.5H, m), 1.90–1.00 ( (f) O-(3-(2-Methylimidazo[4,5-c]pyrid-1-yl)propyl)-5-n-heptyl-delta-valerolactol ether A stirred solution of delta-dodecanolactol (1.95 g, 15 mmol) in dry DCM (100 ml) at 0° C. under argon was treated sequentially with triethylamine (2.1 ml) and trifluoroacetic anhydride (2.1 ml). The mixture was stirred at 0° C. for 15 min, a solution of 3-(2-methylimidazo[4,5-c]pyrid-1-yl)propanol (10.5 g, 30 mmol) was added and the mixture allowed to warm to room temperature over 2 h. The reaction mixture was diluted with DCM (100 ml) and washed with brine (2×50 ml), dried over anhydrous sodium sulphate, filtered and concentrated. Chromatography (silica: 5% methanol in DCM) gave O-(3-(2-methylimidazo [4,5-c]pyrid-1-yl)propyl)-5-n-heptyl-delta-valerolactol ether (a 30:70 mixture of 2 diastereoisomers) as a colourless oil.

i.r. (CDCl$_3$) 1605 cm$^{-1}$ delta$_H$(250 MHz, CDCl$_3$) 8.91 (1H, s), 8.36–8.27 (1H, m), 7.29–7.19 (1H, m), 4.70 (0.7H, br s), 4.31–4.10 (2.3H, m), 3.90–3.78 (0.3H, m), 3.70–3.46 (1.7H, m), 3.31–3.16 (1H, m), 2.59 (3H, s), 2.13–1.10 (20H, m), 0.80 (3H, br t, J 6.0 Hz).

EXAMPLE 2

O-(3-(2-Methylimidazo[4,5-c]pyrid-1-yl)propyl)-5-n-heptyl-gamma-butyrolactol ether

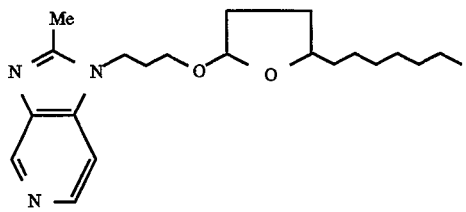

(a) Undecanoic-gamma-lactol

Undecanoic-gamma-lactol was prepared by the procedure of Example 1 Step (e) employing undecanoic-gamma-lactone in lieu of delta-dodecanolactone.

Colourless oil (63% yield).

delta$_H$ (250 MHz, CDCl$_3$) 5.55 (0.5H, dd, J 4.7, 1.8 Hz), 5.47 (0.5H, d, J 3.1 Hz), 4.19 (0.5H, m), 4.00 (0.5H, m), 2.81 (0.5H, br s), 2.73 (0.5H, br s), 2.17–1.28 (16H, m), 0.88 (3H, t, J 6.6 Hz).

(b) O-(3-(2-Methylimidazo[4,5-c]pyrid-1-yl)propyl)-5-n-heptyl-gamma-butyrolactol ether O-(3 -(2-Methylimidazo[4,5-c]pyrid- 1 -yl)propyl)-5-n-heptyl-gamma-butyrolactol ether was prepared by the procedure of Example 1 Step (f) employing undecanoic-gamma-lactol in lieu of delta-dodecanolactol.

Yellow oil (1:1 mixture of two diastereoisomers) (33% yield).

Analysis calculated for $C_{21}H_{33}N_3O_2.0.5H_2O$
Requires C 68.44 H 9.30 N 11.40
Found C 68.34 H 9.15 N 11.32

$delta_H$ (250 MHz, CDCl$_3$) 8.94 (1H, s), 8.39 (1H, d, J 5.6 Hz), 7.29 (1H, d, J 5.5 Hz), 5.05 (0.5H, dd, J 4.9, 2.1 Hz), 4.98 (0.5H, d, J 2.8 Hz), 4.30–4.12 (2H, m), 4.00 (1H, m), 3.71 (1H, m), 3.30 (1H, m), 2.65 (3H, s), 2.17–1.27 (20H, m), 0.87 (3H, t, J 6.7 Hz).

$delta_C$ (62.9 MHz, CDCl$_3$) 141.57, 141.36, 104.87, 104.21, 103.80, 80.92, 78.46, 63.40, 62.88, 41.08, 37.50, 35.44, 33.21, 32.31, 31.78, 29.71, 29.58, 29.44, 29.26, 26.32, 26.09, 22.63, 14.06, 13.84.

EXAMPLE 3

O-(3-(3-Pyridyl)propyl)-5-n-heptyl-gamma-butyrolactol ether

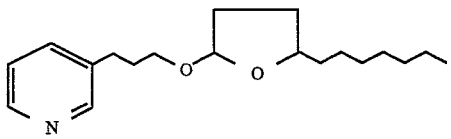

O-(3-(3-Pyridyl)propyl)-5-n-heptyl-gamma-butyrolactol ether was prepared by the procedure of Example 2 Step (b) employing 3-(3-pyridyl)propanol in lieu of 3-(2-methylimidazo[4,5-c]pyrid-1-yl)propanol.

Colourless oil (1:1 mixture of diastereoisomers) (22% yield).

Analysis calculated for $C_{19}H_{31}NO_2.0.2H_2O$
Requires C 73.84 H 10.24 N 4.53
Found C 73.84 H 10.17 N 4.37

$delta_H$ (250 MHz, CDCl$_3$) 8.41 (1H, s), 8.39 (1H, dd, J 4.9, 1.2 Hz), 7.46 (1H, dr, J 7.8, 1.6 Hz), 7.15 (1H, dd, J 7.8, 4.9 Hz), 5.05 (0.5H, dd, J 4.9, 1.9 Hz), 4.98 (0.5H, d, J 3.7 Hz), 3.95 (1H, m), 3.66 (1H, m), 3.33 (1H, m), 2.64 (2H, t, J 7.6 Hz), 2.08–1.22 (20H, m), 0.83 (3H, t, J 6.2 Hz).

$delta_C$ (62.9 MHz, CDCl$_3$) 149.89, 147.18, 137.15, 135.69, 123.08, 103.80, 103.58, 80.60, 77.89, 65.92, 65.66, 37.47, 35.37, 33.17, 32.14, 31.68, 30.93, 29.55, 29.48, 29.33, 29.14, 26.23, 26.01, 22.52, 13.95.

EXAMPLE 4

O-(3 -(2-Methylimidazo[4,5-c]pyrid-1-yl)propyl)-5-n-ethyl-gamma-butyrolactol ether

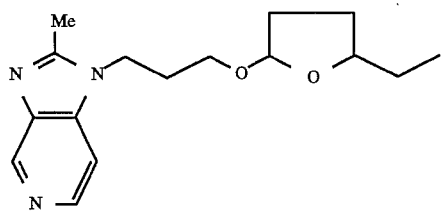

O-(3-(2-Methylimidazo[4,5-c]pyrid-1-yl)propyl)-5-n-ethyl-gamma-butyrolactol ether was prepared by the procedure of Example 2 employing caproic-gamma-lactone in lieu of undecanoic-gamma-lactone.

Yellow oil (1:1 mixture of two diastereoisomers) (4% yield for last step after chromatography over silica gel (5% methanol in DCM).

i.r. (CDCl$_3$) 3200–2700, 1610, 1585, 1515, 1390, 1130 cm$^{-1}$ $delta_H$ (250 MHz, CDCl$_3$) 8.89 (1H, s), 8.29 (1H, d, J 5.5 Hz), 7.20 (1H, d, J 5.5 Hz), 5.00–4.89 (1H, m), 4.25–4.04 (2H, m), 3.95–3.79 (1H, m), 3.70–3.55 (1H, m), 3.30–3.15 (1H, m), 2.57 (3H, s), 2.10–1.70 (5H, m), 1.65–1.30 (3H, m), 0.90–0.78 (3H, m).

$delta_C$ (62.9 MHz, CDCl$_3$) 153.27, 141.46, 141.31, 139.97, 139.71, 104.71, 104.08, 103.64, 82.07, 79.50, 63.23, 62.72, 40.88, 33.07, 32.11, 30.02, 29.54, 28.77, 28.04, 13.64, 10.26, 9.95.

EXAMPLE 5

O-(3-(3-Pyridyl)propyl)-5-n-butyl-gamma-butyrolactol ether

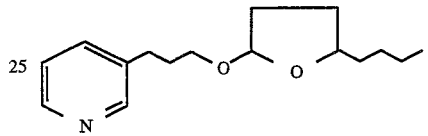

O-(3-(3-Pyridyl)propyl)-5-n-butyl-gamma-butyrolactol ether was prepared by the procedure of Example 2 employing nonanoic-gamma-lactone in lieu of undecanoic-gamma-lactone and 3-(3-pyridyl)propanol in lieu of 3-(2-methylimidazo[4,5-c]pyrid-1-yl)propanol.

Yellow oil (1:1 mixture of two diastereoisomers) (51% yield for last step after chromatography over silica gel (1:2 ethyl acetate/hexane).

Analysis calculated for $C_{16}H_{25}NO_2.0.6H_2O$
Requires C 70.09 H 9.63 N 5.11
Found C 70.27 H 9.26 N 4.94 i.r. (CDCl$_3$) 3200–2750, 1730, 1585, 1420, 1350 cm$^{-1}$ $delta_H$ (250 MHz, CDCl$_3$) 8.40–8.30 (2H, m), 7.40 (1H, br d, J 7.8 Hz), 7.08 (1H, dd, J 7.8, 4.8 Hz), 4.99 (0.5H, dd, J 4.9, 1.7 Hz), 4.92 (0.5H, d, J 4.1 Hz), 4.00–3.83 (1H, m), 3.68–3.53 (1H, m), 3.43–3.20 (1H, m), 2.59 (2H, t, J 7.2 Hz), 2.08–1.68 (4H, m), 1.66–1.11 (8H, m), 0.81 (3H, t, J 6.6 Hz).

$delta_C$ (62.9 MHz, CDCl$_3$) 149.73, 147.00, 136.99, 135.52, 122.92, 103.66, 103.42, 80.41, 77.70, 65.76, 65.48, 37.03, 34.93, 33.02, 31.99, 30.78, 29.42, 29.33, 29.20, 28.29, 28.04, 22.50, 22.44, 13.80.

EXAMPLE 6

O-2-Pyridylmethyl-5-n-butyl-gamma-butyrolactol ether

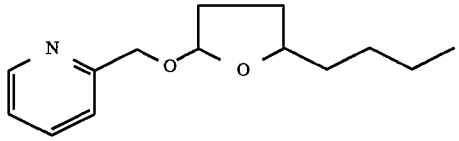

O-2-Pyridylmethyl-5-n-butyl-gamma-butyrolactol ether was prepared by the procedure of Example 2 employing nonanoic-gamma-lactone in lieu of undecanoic-gamma-lactone and 2-pyridylmethanol in lieu of 3-(2-methylimidazo[4,5-c]pyrid-1-yl)propanol.

Yellow oil (1:1 mixture of two diastereoisomers) (59% yield for last step after chromatography over silica gel (1:2 ethyl acetate/hexane).

i.r. (CDCl₃) 3100–2700, 1590, 1570, 1435, 1340 cm⁻¹

$\delta_H$ (250 MHz, CDCl₃) 8.41 (1H, br d, J 4.8 Hz), 7.52 (1H, dt, J 7.8, 1.6 Hz), 7.27 (1H, d, J 7.8 Hz), 7.02 (1H, br t, J 5.0 Hz), 5.20–5.05 (1H, m), 4.70 (1H, d, J 13.3 Hz), 4.55–4.42 (1H, m), 4.03–3.86 (1H, m), 2.08–1.75 (3H, m), 1.70–1.09 (7H, m), 0.77 (3H, t, J 6.6 Hz).

$\delta_C$ (62.9 MHz, CDCl3) 158.52, 148.71, 136.07, 121.77, 121.10, 103.61, 103.20, 80.69, 77.88, 69.60, 69.14, 36.95, 34.83, 33.05, 31.99, 29.11, 28.26, 27.98, 22.41, 13.73.

EXAMPLE 7

O-(3-(3-Pyridyl)propyl)-5-n-heptyl-delta-valerolactol ether

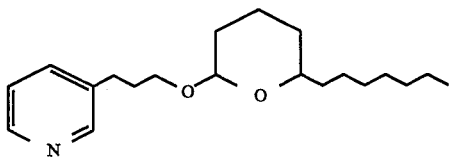

O-(3-(3-Pyridyl)propyl)-5-n-heptyl-delta-valerolactol ether was prepared by the procedure of Example 1 employing 3-(3-pyridyl)propanol in lieu of 3-(2-methylimidazo[4,5-c]pyrid-1-yl)propanol.

Yellow oil (3:7 mixture of two diastereoisomers) (37% yield for last step after chromatography over silica gel (1:3 ethyl acetate/hexane).

i.r. (CDCl₃) 3100–2700, 1725, 1575, 1420, 1120 cm⁻¹

$\delta_H$ (250 MHz, CDCl₃) 8.40 (1H, br s), 8.36 (1H, d, J 4.8 Hz), 7.44 (1H, d, J 7.8 Hz), 7.12 (1H, dd, J 7.5, 4.8 Hz), 4.73 (0.7H, br s), 4.28 (0.3H, m), 3.92–3.80 (0.3H, m), 3.70–3.52 (1.7H, m), 3.41–3.23 (1H, m), 2.78–2.55 (2H, m), 1.95–1.10 (20H, m), 0.81 (3H, t, J 6.0 Hz).

$\delta_C$ (62.9 MHz, CDCl₃) 149.85, 147.15, 137.04, 135.66, 135.54, 123.00, 102.19, 97.04, 77.51, 68.51, 67.05, 65.35, 36.15, 35.82, 31.69, 31.14, 30.83, 29.70, 29.61, 29.55, 29.37, 29.30, 29.11, 25.47, 25.41, 22.47, 22.12, 18.11, 13.89.

EXAMPLE 8

O-2-(4-Methylthiazol-5-yl)ethyl-5-n-butyl-gamma-butyrolactol ether

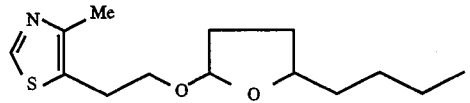

O-2-(4-Methylthiazol-5-yl)ethyl-5-n-butyl-gamma-butyrolactol ether was prepared by the procedure of Example 2 employing nonanoic-gamma-lactone in lieu of undecanoic-gamma-lactone and 2-(4-methylthiazol-5-yl)ethanol in lieu of 3-(2-methylimidazo[4,5-c]pyrid-1-yl)propanol.

Colourless oil (1:1 mixture of two diastereoisomers) (98% yield for last step after chromatography over silica gel (1:3 ethyl acetate/hexane).

i.r. (CDCl₃) 3100–2750, 1540, 1410, 1340 cm⁻¹

$\delta_H$ (250 MHz, CDCl₃) 8.42 (1H, s), 5.00–4.94 (0.5H, m), 4.92–4.86 (0.5H, m), 3.91–3.78 (1H, m), 3.78–3.66 (1H, m), 3.49–3.30 (1H, m), 2.87 (2H, t, J 6.4 Hz), 2.27 (3H, s), 2.00–1.62 (3H, m), 1.60–1.09 (7H, m), 0.81–0.70 (3H, m).

$\delta_C$ (62.9 MHz, CDCl₃) 149.13, 149.03, 148.89, 127.88, 103.58, 103.24, 80.51, 77.72, 66.57, 66.18, 36.81, 34.83, 33.02, 31.92, 29.07, 28.90, 28.26, 27.95, 26.82, 26.70, 22.41, 22.35, 14.59, 13.75.

EXAMPLE 9

2-(3-(3-Pyridyl)propoxy-3a,6,6,9a-tetramethyldodecahydronaphtho [2,1-b]furan

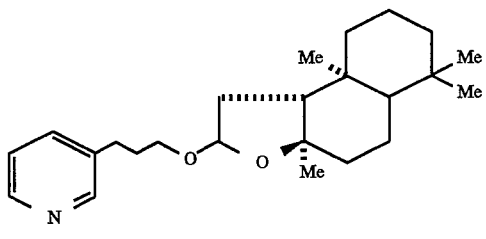

2-(3-(3-Pyridyl)propoxy-3a,6,6,9a-tetramethyldodecahydronaphtho[2,1-b]furan was prepared by the procedure of Example 2 employing (3aR)-(+)-sclareolide in lieu of undecanoic-gamma-lactone and 3-(3-pyridyl)propanol in lieu of 3-(2-methylimidazo [4,5-c]pyrid-1-yl)propanol.

Colourless oil (4:5 mixture of two diastereoisomers) (75% yield for last step after chromatography over silica gel (3:2 ethyl acetate/hexane).

i.r. (CDCl₃) 3000–2840, 1600, 1520, 1345 cm⁻¹

$\delta_H$ (250 MHz, CDCl₃) 8.45–8.41 (2H, m), 7.50 (1H br d, J 7.8 Hz), 7.18 (1H, dd, J 7.8, 4.8 Hz), 5.11–5.06 (1H, m), 3.81–3.65 (1H, m), 3.44–3.29 (1H, m), 2.75–2.52 (2H, m), 2.08–0.90 (19H, m), 0.86 (4H, s), 0.81 (5H, s).

$\delta_C$ (62.9 MHz, CDCl₃) 149.99, 147.24, 137.23, 135.85, 135.76, 123.14, 104.64, 102.92, 82.60, 81.14, 67.26, 66.35, 60.28, 60.16, 57.17, 56.97, 42.38, 40.23, 40.00, 39.81, 39.69, 35.99, 35.91, 33.43, 33.02, 31.14, 30.99, 30.74, 30.61, 29.64, 29.48, 23.53, 22.97, 20.98, 20.73, 20.43, 18.30, 15.21, 15.10.

EXAMPLE 10

O-2-(4-Methylthiazol-5-yl)ethyl-6,7-dimethoxyisochroman-3-ol ether

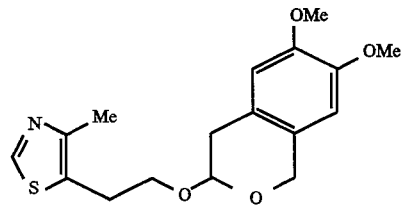

O-2-(4-Methylthiazol-5-yl)ethyl-6,7-dimethoxyisochroman-3-ol ether was prepared by the procedure of Example 2 employing 6,7-dimethoxyisochroman-3-one in lieu of undecanoic-gamma-lactone and 2-(4-methylthiazol-5-yl)ethanol in lieu of 3-(2-methylimidazo[4,5-c]pyrid-1-yl)propanol.

Colourless oil (9% yield for last step after chromatography over silica gel (3:1 ethyl acetate/hexane).

i.r. (CDCl₃) 3100–2750, 1610, 1510, 1250, 1225 cm⁻¹

$\delta_H$ (250 MHz, CDCl₃) 8.51 (1H, s), 6.58 (1H, s), 6.42 (1H, s), 4.98 (1H, t, J 4.7 Hz), 4.63 (1H, d, J 15.0 Hz), 4.54

(1H, d, J 15.0 Hz), 4.07–3.94 (1H, m), 3.81 (3H, s), 3.80 (3H, s), 3.70–3.60 (1H, m), 3.02 (2H, t, J 6.5 Hz), 2.99 (1H, dd, J 16.3, 4.1 Hz), 2.70 (1H, dd, J 16.3, 3.6 Hz), 2.34 (3H, s).

delta$_C$ (62.9 MHz, CDCl$_3$) 149.59, 149.37, 147.94, 147.52, 127.78, 125.49, 122.59, 111.65, 107.03, 97.47, 67.73, 62.38, 55.90, 32.82, 26.89, 14.87.

EXAMPLE 11

O-(3-(2-Methylimidazo[4,5-c]pyrid-1-yl)propyl)-delta-valerolactol ether

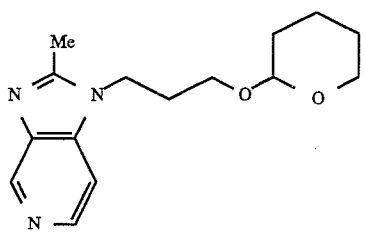

To a stirred solution of 3-(2-methylimidazo[4,5-c]pyrid-1-yl)propanol (3.0 g, 0.016 mol) and dihydopyran (2.3 ml, 0.025 mol) in dry DCM at room temperature was added a catalytic quantity of p-toluenesulphonic acid. After stirring overnight solid sodium carbonate was added and the mixture filtered through celite and concentrated. The residue was purified by chromatography over silica gel (6% methanol in DCM) to give O-(3-(2-methylimidazo[4,5-c]pyrid-1-yl) propyl)-delta-valerolactol ether as a colourless oil (500 mg,12%).

i.r. (CDCl$_3$) 3050–2800, 1735, 1610, 1585, 1390 cm$^{-1}$ delta$_H$ (250 MHz, CDCl$_3$) 8.96 (1H, br s), 8.36 (1H, br d, J 4.6 Hz), 7.28 (1H, br d, J 4.8 Hz), 4.54–4.47 (1H, m), 4.40–4.15 (2H, m), 3.89–3.71 (2H, m), 3.55–3.41 (1H, m), 3.40–3.27 (1H, m), 2.65 (3H, s), 2.17–2.00 (2H, m), 1.80–1.64 (2H, m), 1.62–1.46 (4H, m).

delta$_C$ (62.9 MHz, CDCl$_3$) 153.47, 141.63, 141.45, 140.14, 99.32, 63.48, 62.91, 41.00, 30.73, 29.67, 25.28, 19.84, 13.78.

EXAMPLE 12

Inhibition of [$^3$H]-PAF receptor binding

The inhibition of [$^3$H]-PAF binding to human platelet plasma membranes by compounds of general formula I was determined by isotopic labelling and filtration techniques. Platelet concentrates were obtained from a hospital blood bank. These platelet concentrates (500–2500 ml.) were centrifuged at 800 rpm for 10 minutes in a SORVALL RC3B centrifuge to remove the red blood cells present. (The word SORVALL is a trade mark.) The supernalant was subsequently centrifuged at 3,000 rpm in a SORVALL RC3B centrifuge to pellet the platelets present. The platelet rich pellets were resuspended in a minimum volume of buffer (150 mM NaCl, 10 mM Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a band between the plasma and the Ficoll were removed, resuspended in the above buffer and centrifuged at 3,000 rpm for 10 minutes in a SORVALL RT6000 centrifuge. The pelleted platelets were resuspended in buffer (10 mM Tris, 5mM MgCl$_2$, 2 mM EDTA, pH 7.0), snap freezed in liquid N$_2$ and allowed to thaw slowly at room temperature in order to lyse the platelets. The latter step was repeated at least 3 times to ensure proper lysis. The lysed platelets were centfifuged at 3,000 rpm for 10 minutes in a SORVALL RT6000 centrifuge and resuspended in buffer. The latter step was repeated twice in order to remove any cytoplasmic proteins which may hydrolyse the platelet activating factor (PAF) receptor. The prepared platelet membranes may be stored at –70° C. After thawing the prepared membranes were centrifuged in a SORVALL RT6000 at 3,000 rpm for 10 minutes and resuspended in assay buffer.

The assay was conducted by preparing a series of Tris-buffered solutions of the selected antagonist of predetermined concentrations. Each of these solutions contained [$^3$H]-PAF (0.5 nM; 1-O-[$^3$H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10mm Tris, 5mM MgCl$_2$, pH 7.0, 0.25% BSA) to make the final volume 1 ml. Incubation was initiated by the addition of 100 μg of the isolated membrane fraction to each of the above solutions at 0° C. Two control samples, one (C1) which contained all the ingredients described above except the antagonist and the other (C2) contains C1 plus a 1000-fold excess of unlabelled PAF, were also prepared and incubated simultaneously with the test samples. After 1 hour incubation, each solution was filtered rapidly under vacuo through a WHATMAN GF/C glass fibre filter in order to separate unbound PAF from bound PAF. (The word WHATMAN is a trade mark.) The residue in each case was rapidly washed 4 times with 5 ml cold (4oC) Tris-buffer solution. Each washed residue was dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB", the percent inhibition of each test antagonist can be determined by the following equation:

% Inhibition=[(TB–TBA)/SB]×100 where the specific binding SB=TB–NSB

Table 1 lists results from this assay for inhibition of [$^3$H]-PAF receptor binding for illustrative examples of the compounds of this invention.

TABLE 1

Results for inhibition of [$^3$H]-PAF receptor binding

| Example | Inhibition of [$^3$H]-PAF binding IC$_{50}$ μM |
|---|---|
| 1 | 0.08 |
| 2 | 0.12 |

EXAMPLE 13

Inhibition of PAF-induced hypotension in the rat

The activity of the compounds of general formula I is also demonstrated in vivo by their ability to reverse the hypotension caused by an infusion of PAF in rats. Male Sprague-Dawley rats (300–400 g) were anaesthetised with a mixture of sodium pentobarbitone, 22.5 mg/kg and thiopental 62.5 mg/kg. Through a midline incision in the neck, the trachea was cannulated and the animals breathed spontaneously. A carotid artery was cannulated for the measurement of blood pressure and this signal was used to trigger a rate meter to measure heart rate. Both jugular veins were cannulated: one for the infusion of PAF and the other for the bolus administration of test compounds.

PAF, 100 ng/kg/min was infused i.v. until a sustained fall in mean blood pressure of 50 mmHg was achieved. Test compounds were administered i.v. as a bolus and resulted in a dose dependent reversal of the PAF induced hypotension. The peak of this reversal was measured and the dose to cause a 50% reversal of the hypotensive PAF response ($ED_{50}$) calculated by straight line interpolation and the results are presented in Table 2.

TABLE 2

| Results for inhibition of PAF-induced hypotension in the rat | |
| --- | --- |
| Example | $ED_{50}$ (µg/kg i.v.) |
| 2 | 2.1 |

We claim:

1. A compound of general formula I:

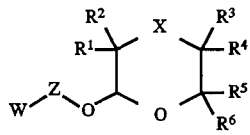

wherein:

W represents a 5- or 6-membered aromatic heterocyclic ring containing one or more non-quaternised sp2 nitrogen atoms in its ring, which heterocyclic ring may be optionally fused to a benzene ring or to a further 5- or 6-membered aromatic heterocyclic ring containing one or more nitrogen atoms, wherein at least one of the said heterocyclic rings may also contain an oxygen or sulphur atom, and wherein any of the rings may be optionally substituted with one or more substituents selected from the group consisting of —$C_1$-$C_6$ alkyl, —$OC_1$-$C_6$ alkyl, halo, —$CF_3$ and —CN;

Z represents a) a divalent alkanediyl group from 1 to 8 carbon atoms which may be a straight or branched-chain, wherein the said group is either unsubstituted or substituted by one or more substituents selected from the group consisting of hydroxy, —$OC_1$-$C_6$ alkyl, —$SC_1$-$C_6$ alkyl and halo; or b) a divalent alkenediyl or alkynediyl group from 2 to 8 carbon atoms which may be straight or branched-chain, wherein the said group is either unsubstituted or substituted by one or more substituents selected from the group consisting of hydroxy, —$OC_1$-$C_6$ alkyl, —$SC_1$-$C_6$ alkyl and halo;

$R^1$, $R^2$, $R^3$, $R^4$, $R^5$, and $R^6$ each represents a hydrogen atom, a —$C_1$-$C_{18}$ alkyl or a —$C_2$-$C_{18}$ alkenyl group;

or $R^3$ or $R^5$ together with the carbon atoms to which they are attached can form a five to ten membered monocycloalkyl or bicycloalkyl ring which may be optionally substituted with one or more substituents selected from —$C_1$-$C_6$ alkyl, —$OC_1$-$C_6$ alkyl, halo, —$CF_3$ and —CN;

or $R^3$, $R^4$ and $R^5$, $R^6$ and the carbon atoms to which they are attached form a phenyl ring which may be optionally substituted with one or more substituents selected from the group consisting of —$C_1$-$C_6$ alkyl, —$OC_1$-$C_6$ alkyl, halo, —$CF_3$ and —CN;

X represents a bond, an oxygen atom, a sulphur atom, a —NH— group, a —N($C_1$-$C_6$ alkyl)— group, a —($CH_2$)$_n$— group or a —$CR^7R^8$— group;

n represents an integer of 1, 2 or 3;

$R^7$ and $R^8$ each represents a —$C_1$-$C_{18}$ alkyl or a —$C_2$-$C_{18}$ alkenyl group;

or $R^3$ and $R^7$ together with the carbon atoms to which they are attached can form a five to ten membered monocycloalkyl or bicycloalkyl ring which may be optionally substituted with one or more substituents selected from the group consisting of —$C_1$-$C_6$ alkyl, —$OC_1$-$C_6$ alkyl, halo, —$CF_3$ and —CN;

or $R^3$, $R^4$ and $R^7$, $R^8$ and the carbon atoms to which they are attached form a phenyl ring which may be optionally substituted with one or more substituents selected from the group consisting of —$C_1$-$C_6$ alkyl, —$OC_1$-$C_6$ alkyl, halo, —$CF_3$ and —CN;

or a pharmaceutically or veterinarily acceptable acid addition salt or hydrate thereof.

2. A compound as claimed in claim 1, in which W represents a pyridyl, thiazolyl or an imidazo [4,5 -c]pyrid-1-yl group.

3. A compound as claimed in claim 1, wherein Z represents an alkanediyl group.

4. A compound as claimed in claims 1, wherein $R^1$ represents a hydrogen atom.

5. A compound as claimed in claim 1, wherein $R^2$ represents a hydrogen atom.

6. A compound as claimed in claim 1, wherein $R^3$ represents a hydrogen atom.

7. A compound as claimed in claim 1, wherein $R^4$ represents a hydrogen atom.

8. A compound as claimed in claim 1, wherein $R^5$ represents a hydrogen atom or together with $R^3$ and the carbon atoms to which they are attached form a five to ten membered monocycloalkyl or bicycloalkyl ring.

9. A compound as claimed in claim 1, wherein $R^6$ represents a hydrogen atom or a –$C_1$-$C_{18}$ alkyl group.

10. A compound as claimed in claim 1, wherein X is a bond or a —($CH_2$)$_n$— group.

11. A compound as claimed in claim 10, wherein n is an integer of 1.

12. A compound as claimed in claim 1, wherein X is a $CR^7R^8$ group and $R^7$ and $R^8$ represent together with $R^3$ and $R^4$ and the carbon atoms to which they are attached a phenyl ring.

13. A compound selected from the group consisting of:

O-(3- (2 -Methylimidazo [4,5-c]pyrid-1-yl)propyl) -5-n-heptyl-delta-valero-lactol ether, O-(3 - (2 -Methyl imidazo[4,5-c]pyrid-1-yl)propyl)-5-n-heptyl-gamma-butyrolactol ether, O-(3-(3-Pyridyl)propyl)-5-n-heptyl-gamma-butyrolactol ether, O-(3-(2-Methylimidazo[4,5-c]pyrid-1-yl)propyl)-5-n-ethyl-gamma-butyrolactol ether, O-(3-(3-Pyridyl)propyl )-5-n-butyl-gamma-butyrolactol ether, O-2-Pyridylmethyl-5-n-butyl-gamma-butyrolactol ether, O-(3-(3-Pyridyl)propyl)-5-n-heptyl-delta-valerolactol ether, O-2-(4-Methylthiazol-5-yl)ethyl-5-n-butyl-gamma-butyrolactol ether, 2-(3-(3-Pyridyl)propoxy-3a,6,6,9a-tetramethyldodecahydro-naphtho[2,1-b]furan, O-2-(4-Methylthiazol-5-yl)ethyl-6,7-dimethoxyisochroman-3-ol ether, and O(3-(2-Methylimidazo[4,5-c]pyrid-1-yl) propyl) -delta-valerolactol ether, or a pharmaceutically or veterinarily acceptable acid addition salt of such a compound.

14. A pharmaceutical or veterinary formulation comprising a compound as claimed in any one of claim 1 and a pharmaceutically and/or veterinarily acceptable carrier.

15. A process for preparing a compound of general formula I as defined in claim 1, the process comprising:

a) treating a lactol derivative represented by the general formula II

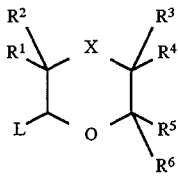

wherein $R^1$, $R^2$, $R^3$, $R^4$, $R^5$, $R^6$ and X are as defined in general formula and L is fluoro, chloro, bromo, iodo, hydroxy, —$OC_1$-$C_6$ alkyl, benzoxy, acetoxy, —OC(NH)$CCl_3$, —$SO_2Ph$, —$SC_1$-$C_6$ alkyl or SPh with an alcohol of the general formula III

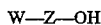

W—Z—OH   III wherein W and Z are as defined in general formula I;

b) treating a lactol derivative represented by the general formula II, wherein $R^1$, $R^2$, $R^3$, $R^4$, $R^5$, $R^6$ and X are as defined in general formula I and L is hydroxy with a halide of general formula IV

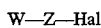

W—Z—Hal   IV wherein W and Z are as defined in general formula I and Hal is fluoro, chloro, bromo or iodo;

c) treating an unsaturated lactol derivative represented by the general formula V

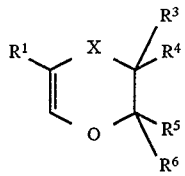

wherein $R^1$, $R^3$, $R^4$, $R^5$, $R^6$ and X are as defined in general formula I with an alcohol of general formula III and an acid catalyst;

d) reducing an unsaturated lactol ether of general formula VI

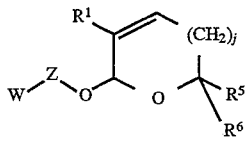

wherein W, Z, $R^1$, $R^5$, and $R^6$ are as defined in general formula I and j is an integer from 1 to 3; or e) treating a sulphonyl cyclic ether of general formula VII

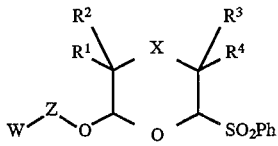

wherein W, Z, $R^1$, $R^2$, $R^3$, $R^4$ and X are as defined in general formula I, with a Grignard reagent of general formula VIII

$R^6MgBr$   VIII wherein $R^6$ is as defined in general formula I but is not hydrogen; and f) optionally after any of steps (a) to (e) converting a compound of general formula I so formed into another compound of general formula I.

16. A method for the treatment or prophylaxis of diseases or conditions mediated by platelet activating factor, the method comprising administering to a patient an effective amount of a compound as claimed in claim 1.

* * * * *